United States Patent
Rudolph

(10) Patent No.: US 7,208,167 B2
(45) Date of Patent: Apr. 24, 2007

(54) TREATMENT OF HEPATITIS C WITH THYMOSIN AND PEPTIDE COMBINATION THERAPY

(75) Inventor: Alfred R. Rudolph, Los Altos Hills, CA (US)

(73) Assignee: SciClone Pharmaceuticals, Inc., San Mateo, CA (US)

( * ) Notice: Subject to any disclaimer, the term of this patent is extended or adjusted under 35 U.S.C. 154(b) by 93 days.

(21) Appl. No.: 10/359,536

(22) Filed: Feb. 7, 2003

(65) Prior Publication Data

US 2003/0185799 A1    Oct. 2, 2003

Related U.S. Application Data

(63) Continuation-in-part of application No. PCT/US01/41549, filed on Aug. 6, 2001, which is a continuation-in-part of application No. PCT/US01/41550, filed on Aug. 6, 2001.

(60) Provisional application No. 60/223,312, filed on Aug. 7, 2000, provisional application No. 60/223,317, filed on Aug. 7, 2000.

(51) Int. Cl.
    *A61K 38/00*    (2006.01)
(52) U.S. Cl. .................. 424/278.1; 530/300; 514/2; 514/12; 424/85.4; 424/130.1
(58) Field of Classification Search .......... 514/2, 514/12; 424/85.4, 130.1, 278.1, 287.1; 530/300
    See application file for complete search history.

(56) References Cited

U.S. PATENT DOCUMENTS

| | | | |
|---|---|---|---|
| 5,762,923 A | 6/1998 | Gross et al. | |
| 5,849,696 A | 12/1998 | Chretien et al. | |
| 5,849,800 A | 12/1998 | Smith | |
| 5,849,860 A | 12/1998 | Hakimi et al. | |
| 5,869,253 A | 2/1999 | Draper | |
| 5,908,621 A * | 6/1999 | Glue et al. .......... | 424/85.7 |
| 5,951,974 A | 9/1999 | Gilbert et al. | |
| 6,001,799 A | 12/1999 | Chretien et al. | |
| 6,172,046 B1 | 1/2001 | Albrecht | |
| 6,177,074 B1 | 1/2001 | Glue et al. | |
| 6,200,952 B1 | 3/2001 | Horwitz | |

FOREIGN PATENT DOCUMENTS

| | | | |
|---|---|---|---|
| CN | 1261806 A | 8/2000 | |
| WO | WO 94/13314 A1 | 6/1994 | |
| WO | WO 94/20131 A | 9/1994 | |
| WO | WO 99/15194 A1 | 4/1999 | |
| WO | WO 99/64016 A1 | 12/1999 | |
| WO | WO 00/37110 A2 | 6/2000 | |

OTHER PUBLICATIONS

Sherman et al., Combination Therapy With Thymosin alpha 1 and Interferon. Hepatology 1998 vol. 27, pp. 1128-1135.*
Weiland, Ola, Interferon and ribavirin combination therapy. Forum 2000, vol. 10, No. 1, pp. 22-28.*
Rosen et al., Molecular Medicine Today, vol. 5, pp. 393-399, 1999.*
Lee, William M., "Therapy of Hepatitis C: Interferon Alfa-2a Trials", *Hepatology*, vol. 26, No. 3, Suppl. 1, Sep. 1997, pp. 89S-95S.
Sherman, Kenneth E. et al., "Combination Therapy with Thymosin α1 and Interferon for the Treatment of Chronic Hepatitis C Infection: A Randomized, Placebo-Controlled Double-Blind Trial", *Hepatology*, vol. 27, No. 4, Apr. 1998, pp. 1128-1135.
Weiland, Ola, "Interferon and Ribavirin Combination Therapy: Indications and Schedules", *Forum*, 2000, vol. 10, No. 1, 5 pages.
Kita, Y, et al., "Characterization of a polyethylene glycol conjugate of recombinant human interferon-gamma", *Drug Design and Delivery*, vol. 6, No. 3, (1990), 157-167.
Sherman, K., et al. "Combination therapy with thymosin a1 and interferon for the treatment of chronic hepatitis C infection: a randomized, placebo-controlled double-blind trial", *Hepatology*, 27(4):1128-1135, 1998.
Ambrosch, A. et al., :Characteristics of the Hepatitis C virus and viral predictors of therapeutic response, *Medizinische Klinik* (Munich, Germany: 1983), vol. 94, No. 11, Nov. 15, 1999, pp. 626-632.
Naylor, P.H., "Zadaxin (Thymosin A1) for the Treatment of Viral Hepatitis," *Expert Opinion on Investigational Drugs*, Ashley Publications Ltd., London, GB, vol. 8, No. 3, Mar. 1999, pp. 281-287.
Rosen, Hugo R. et al., "Hepatitis C virus: current understanding and prospects for future therapies," *Molecular Medicine Today*, vol. 5, No. 98, Sep. 1999, pp. 393-399.

* cited by examiner

Primary Examiner—Bruce R. Campell
Assistant Examiner—Myron G. Hill
(74) Attorney, Agent, or Firm—Rothwell, Figg, Ernst & Manbeck, PC

(57) ABSTRACT

A method and pharmaceutical combination for treating hepatitis C by administering to a hepatitis C patient an effective amount of at least one alpha thymosin peptide, in combination with administration to the hepatitis C patient of an effective amount of at least one interferon, and optionally in combination with administration of at least one antiviral agent such as ribavirin.

7 Claims, No Drawings

TREATMENT OF HEPATITIS C WITH THYMOSIN AND PEPTIDE COMBINATION THERAPY

CROSS REFERENCE TO RELATED APPLICATIONS

This application is a continuation-in-part of PCT/US01/41549, filed Aug. 6, 2001, which claims benefit from U.S. Provisional Application Ser. No. 60/223,312, filed Aug. 7, 2000. This application also is a continuation-in-part of PCT/US01/41550, filed Aug. 6, 2001, which claims benefit from U.S. Provisional Application Ser. No. 60/223,317, filed Aug. 7, 2000.

BACKGROUND OF THE INVENTION

1. Field of the Invention

This invention relates generally to the pharmacological treatment of hepatitis C virus infection in patients.

2. Description of the Related Art

Hepatitis C virus (HCV) is the putative agent in the majority of cases of post-transfusion acquired hepatitis. Despite improvement in the quality of the blood-donor pool and the implementation of testing of donated blood, the incidence of acute infection among persons receiving transfusions is still significant. Chronic hepatitis develops in at least half the patients with acute HCV infection (representing about 90% of patients with non-A, non-B hepatitis (NANB)), and cirrhosis develops in at least 20% of this group. A variety of drugs have been evaluated with the aim of halting or slowing the progression of HCV-related diseases.

Certain studies have shown $\alpha$-interferon (IFA) to have positive effects. See U.S. Pat. No. 5,849,696. Interferons are a family of naturally occurring small proteins and glycoproteins produced and secreted by most nucleated cells in response to viral infection as well as other antigenic stimuli. Interferons render cells resistant to viral infection and exhibit a wide variety of actions on cells. They exert their cellular activities by binding to specific membrane receptors on the cell surface.

One of the principal factors which has been found to severely limit the use of interferon has been the fact that it elicits an immunogenic response in the circulatory system. This response being the production of antibodies to the interferon by the host into which they are injected. This effect causes the flu-like symptoms reported as side effects to interferon therapy and also causes the destruction of the interferon thereby requiring larger doses for a therapeutic effect. It has been found that interferon (like other polypeptides used for therapeutic purposes) can be coupled to polymers which are substantially non-immunogenic and retain the substantial proportion of their desired physiological activity. U.S. Pat. No. 6,177,074 discloses a method of treating chronic hepatitis C virus infection by administering 12,000 molecular weight polyethylene glycol conjugated interferon $\alpha$ ("PEG$_{12,000}$–IFN $\alpha$"). It was found that this treatment provides improved therapeutic benefits while substantially reducing or eliminating entirely the undesirable side effects normally associated with interferon $\alpha$ treatment regimes.

Another class of polypeptide immune modifiers derived from the thymus gland, the thymosins, has been shown to trigger maturational events in lymphocytes, to augment T-cell function and to promote reconstitution of immune defects. Thymosin alpha 1 (TA1) is a 28 amino acidic polypeptide with a molecular weight of 3100 that has potent immunologic activity, including stimulation of $\alpha$- and $\gamma$-interferon production, increasing macrophage migration inhibitory factor production, inducing expression of T-cell markers, IL-2 receptors, and improving T-cell helper cell activity. The isolation, characterization and use of THN$\alpha_1$ is described, for example, in U.S. Pat. No. 4,079,127.

Thymosin therapy may also be used in combination with interferon therapy, thereby combining the immune system potentiating effect of thymosins with the anti-viral effects of the interferons. This is disclosed in U.S. Pat. 5,849,696.

Various antiviral agents have been used as sole therapy agents in an attempt to treat chronic hepatitis C infection, including acyclovir, vidarabine, and adenine arabinoside. Sole therapy with these antiviral agents generally has been unsuccessful, either because the agent was highly toxic or resulted in some inhibition of viral replication initially, but failed to sustain viral replication inhibition long-term. See e.g. Alexander, G. J. M. et al., American J. Med. (1988), 85-2A: 143–146.

There remains an important need for therapy for hepatitis C that efficiently and with fewer side effects attacks the virus and modulates the immune response system and reduces the frequency of relapse.

SUMMARY OF THE INVENTION

The present invention provides a method and pharmaceutical combination for treating hepatitis C infection in mammals comprising administering to a hepatitis C-infected mammal an effective amount of at least one alpha thymosin peptide or an effective amount of at least one alpha thymosin peptide fragment, in combination with the administration of an effective amount of an interferon. Certain embodiments include administration of an antiviral agent.

DETAILED DESCRIPTION OF THE INVENTION

According to one embodiment, the present invention provides a method and pharmaceutical combination for treating hepatitis C infection in mammals comprising concurrently or sequentially administering to a hepatitis C-infected patient a pharmaceutical dosage unit containing a therapeutically effective amount of at least one alpha thymosin peptide in combination with an amount of an interferon effective to treat hepatitis C while simultaneously substantially reducing or eliminating side effects normally associated with the administration of interferon. In preferred embodiments, the drug regimen includes thymosin $\alpha$-1, pegylated interferon $\alpha$ and administration of a pharmaceutical dosage unit containing an effective amount of an antiviral agent, preferably a nucleoside analog. In particularly preferred embodiments the nucleoside analog is an antiviral-effective amount of ribavirin.

Pegylated interferon is interferon conjugated to a polymer. Conjugation may be accomplished by various linkers known in the art. The molecular weight of the polymer, which is preferably polyethylene glycol, may range from 300 to 300,000 Daltons. One or more polymers may be conjugated to the interferon.

The present invention is applicable to alpha thymosin peptides including naturally occurring TA1 as well as synthetic TA1 and recombinant TA1 having the amino acid sequence of naturally occurring TA1, amino acid sequences substantially similar thereto, or an abbreviated sequence form thereof, and their biologically active analogs having substituted, deleted, elongated, replaced, or otherwise modified sequences which possess bioactivity substantially similar to that of TA1, e.g., a TA1 peptide having sufficient amino acid homology with TA1 such that it functions in substantially the same way with substantially the same activity as TA1.

The terms "thymosin α1", "Tα1" and "TA1" refer to peptides having the amino acid sequence disclosed in U.S. Pat. No. 4,079,137, the disclosure of which is incorporated herein by reference.

Antiviral-effective amounts of alpha thymosin peptides are hepatitis C virus-reducing amounts of alpha thymosin peptides which may be dosage units comprising about 0.5–100 mg alpha thymosin peptides. Exemplary dosages are 1.6 mg and 3.2 mg of alpha thymosin peptides.

Separate dosage units of alpha thymosin peptides, interferon and an amount of at least one antiviral agent can be administered to the patient every other day, but preferably once or twice a week. Doses of interferon and alpha thymosin peptides may be administered by subcutaneous injection. According to one aspect of this embodiment of the present invention, the dosage unit comprising alpha thymosin peptides is administered to the patient on a routine basis. For example, the dosage unit can be administered once daily, weekly, monthly, etc. The dosage unit may be administered one to seven times a week. According to one embodiment, 3.2 mg alpha thymosin peptides is administered two times per week.

According to another aspect of the invention, the administration of the dosage unit comprising alpha thymosin peptides is administered for a period of time, concurrent with administration of pegylated interferon sufficient to reduce or eliminate HCV infection in the patient.

In the practice of the invention, preferred pegylated interferon alpha-1a or -2b conjugates may be administered to patients infected with the hepatitis C virus. Use of PEG-IFN alpha-2a is preferred.

The amount of the pegylated interferon conjugate administered to treat hepatitis C is based on the interferon activity of the polymeric conjugate. It is an amount that is sufficient in conjunction with administration of alpha thymosin peptides to significantly affect a positive clinical response while maintaining diminished side effects. In preferred embodiments, the amount of pegylated interferon alpha which may be administered is in the range of at least about 0.25 µg–900 µg in single or divided doses depending on the activity of the pegylated interferon. For example, a dosage of 180 µg of PEG-INF alpha-2a may be administered.

Administration of the described dosages may be up to seven times per week, but is preferably once or twice a week. Doses can occur for a length of time in conjunction with administration of alpha thymosin peptides and are administered preferably over a 24 week period by subcutaneous injection.

Administration of the dose can be intravenous, subcutaneous, intramuscular, or any other acceptable method. Based on the judgment of the attending clinician, the amount of drug administered and the treatment regimen used will, of course, be dependent on the age, sex and medical history of the patient being treated, the neutrophil count (e.g. the severity of the neutrophenia), the severity of the specific disease condition and the tolerance of the patient to the treatment as evidenced by local toxicity and by systemic side-effects. Dosage amount and frequency may be determined during initial screenings of neutrophil count.

In an exemplary embodiment, alpha thymosin peptide is administered by subcutaneous injection twice weekly in pharmaceutical dosage units within the range of about 0.5–4.5 mg, preferably about 1.6–3.2 mg (e.g., about 3.2 mg). In conjunction with the administration to the patient of about 0.25–900 µg of pegylated interferon alpha once daily.

Although the preferred embodiment speaks in terms of pegylated interferon alpha, other pegylated anti-HCV-effective interferons such as β and γ-interferons may be advantageously used in this invention.

According to another aspect of this embodiment, the administration of the dosage unit comprising alpha thymosin peptides is administered for a period of time, concurrent with administration of pegylated interferon and an amount of at least one antiviral agent, sufficient to reduce or eliminate HCV infection in the patient.

Antiviral agents of the present invention which are pyrimidine nucleoside analogs include ddI, ddC, AZT and FIAU (fluoro-iodo-arabionfuranosyl-uracil) (see Table A below). Antiviral agents of the present invention which are purine nucleoside analogs include acyclovir, ribavirin, ganciclovir, and vidarabine (see Table A below). Similarly, acyclovir and other purine analogs act as polynucleotide chain terminators. These analogs act as faulty substrates, thus preventing DNA transcription. The mode of action of ribavirin is most likely interference with viral mRNA, resulting in inhibition of viral replication.

The antiviral agents of the present invention, are given in an appropriate pharmaceutical dosage formulation. The pyrimidine nucleoside analogs of the present invention can be given intravenously or orally to hepatitis C-infected subjects at effective viral inhibiting dosages and according to regimens appropriate to the severity of the disease and clinical factors. However, when given in combination with a thymosin, a lower daily dosage for a subject can be devised according to the clinical parameters and tests listed below. Those with skill in the art will, without undue experimentation, be able to devise dosages depending on the clinical condition of patients and the parameters discussed below.

An "inhibitorily effective amount" of an antiviral drug or agent is an amount of the drug which inhibits HCV virus replication, measured by a decrease in viral DNA in the blood, as measured by PCR or other method known in the art.

In a particularly preferred embodiment, an inhibitorily effective amount of ribavirin is the antiviral agent included in the combination chemotherapy regimen.

According to preferred embodiments, dosage units comprising amounts of ribavirin is the antiviral agent included in the combination chemotherapy regimen.

According to preferred embodiments, dosage units comprising amounts of ribavirin which, in conjunction with administration of alpha thymosin peptides, and pegylated interferon are effective in reducing hepatitis C virus in a patient, are included within the dosage range of abut 100–2000 mg, preferably 400–1800 mg. Even more preferably, ribavirin in the amount of 800–120 mg may be administered.

The dosage unit comprising the antiviral agent can be administered to the patient on a routine basis, for example, the dosage unit can be administered once daily, more than once daily (e.g., two, three or more times daily), weekly, monthly, etc. More preferably, the dosage unit is administered three times daily. Administration of the antiviral agent dosage unit can occur for a length of time, in conjunction with administration of thymosin α1, and pegylated interferon effective to reduce or eliminate HCV infection in the patient. Preferably, such administration occurs for at least about six months, and most preferably, for about 6–12 months.

In preferred embodiments alpha thymosin peptides is administered by subcutaneous injection twice weekly in pharmaceutical dosage units within the range of about 0.5–4.5 mg, preferably about 1–4 mg (e.g., about 1.6 mg or about 3.2 mg), in conjunction with subcutaneous injection to the patient of about 180 μg of pegylated alpha-2a and 300 mg ribavirin three times daily.

However, it is to be understood that pharmaceutical dosage units containing alpha thymosin peptides, pegylated interferon and an antiviral agent may be formulated in any suitable manner, utilizing any suitable pharmaceutically acceptable carrier (e.g., saline or water for injection), for administration by any suitable route.

In preferred embodiments in which both pegylated interferon and ribavirin are utilized with alpha thymosin peptides there is a lower probability for the HCV virus to mutate, thereby creating a low viral load period of long duration for the enhanced immunological response of alpha thymosin peptides to act.

According to another aspect of the invention, the administration of the dosage unit comprising alpha thymosin peptides is administered for a period of time, concurrent with administration of interferon sufficient to reduce or eliminate HCV infection in the patient and an inhibitorily effective amount of an antiviral drug or agent.

In the practice of the invention, preferred interferon α conjugates may be administered to patients infected with the hepatitis C virus. Use of interferon α-2b is preferred.

The amount of the interferon administered to treat hepatitis C is an amount that is sufficient in conjunction with administration of alpha thymosin peptides to significantly affect a positive clinical response while maintaining diminished side effects. In preferred embodiments, the amount of interferon α-2b which may be administered is in the range of 1 MU–3 MU.

Administration of the described dosages may be up to seven times per week, but is preferably once or twice a week. Doses can occur for a length of time in conjunction with administration of alpha thymosin peptides and are administered preferably over a 24 week period by subcutaneous injection.

Administration of the dose can be intravenous, subcutaneous, intramuscular, or any other acceptable method. Based on the judgment of the attending clinician, the amount of drug administered and the treatment regimen used will, of course, be dependent on the age, sex and medical history of the patient being treated, the neutrophil count (e.g. the severity of the neutropenia), the severity of the specific disease condition and the tolerance of the patient to the treatment as evidenced by local toxicity and by systemic side-effects. Dosage amount and frequency may be determined during initial screenings of neutrophil count.

For any route of administration, divided, single or multiple dosage units may be used. For example, when a subcutaneous injection is used to deliver, for example, 3 MU of interferon over one week, two injections of 1.5 MU at 0 and 72 hours may be administered.

In an exemplary embodiment, alpha thymosin peptide is administered by subcutaneous injection twice weekly in pharmaceutical dosage units within the range of about 0.5–4.5 mg, preferably about 1.6–3.2 mg (e.g., about 3.2 mg). In conjunction with the administration to the patient of about 1 MU–3 MU of interferon once daily.

Although the preferred embodiment speaks in terms of interferon α, other anti-HCV-effective interferons such as α2a, β and γ-interferons may be used in this invention.

In a particularly preferred embodiment, an inhibitorily effective amount of ribavirin is the antiviral agent included in the combination chemotherapy regimen.

According to preferred embodiments, dosage units comprising amounts of ribavirin which, in conjunction with administration of alpha thymosin peptides, and interferon are effective in reducing hepatitis C virus in a patient, are included within the dosage range of about 100–2000 mg, preferably 400–1800 mg. Even more preferably, ribavirin in the amount of 800–1200 mg may be administered.

The dosage unit comprising the antiviral agent can be administered to the patient on a routine basis, for example, the dosage unit can be administered once daily, more than once daily (e.g., two, three or more times daily), weekly, monthly, etc. Most preferably, the dosage unit is administered three times daily. Administration of the antiviral agent dosage unit can occur for a length of time, in conjunction with administration of alpha thymosin peptides, and interferon effective to reduce or eliminate HCV infection in the patient. Preferably, such administration occurs for at least about six months, and most preferably, for about 6–12 months.

In preferred embodiments alpha thymosin peptides are administered by subcutaneous injection twice weekly in pharmaceutical dosage units within the range of about 0.5–4.5 mg, preferably about 1–4 mg (e.g., about 1.6 mg or about 3.2 mg), in conjunction with subcutaneous injection to the patient of about 1 MU–3 MU of interferon α and 300 mg ribavirin orally, three times daily.

However, it is to be understood that pharmaceutical dosage units containing alpha thymosin peptides, interferon and an antiviral agent may be formulated in any suitable manner, utilizing any suitable pharmaceutically acceptable carrier (e.g., saline or water for injection), for administration by any suitable route.

Interferons are known to affect a variety of cellular functions, including DNA replication and RNA and protein synthesis in both normal and infected cells. Alpha thymosin peptides including Thymosin α-1 are immune system modulators that can play an instrumental role in the activation of host immunity mechanisms for the treatment of chronic hepatitis C. Anti-viral agents such as nucleoside analogs are not viricidal, i.e., they do not kill viruses. They suppress the replication (reproduction) of the viruses so that the viral load goes down to unmeasurable levels. However, the viruses may not be eliminated altogether by nucleoside analogs alone. The use of interferon and ribavirin with alpha thymosin peptides lowers the probability that HCV virus will mutate, thereby creating a low viral load period of long duration for the enhanced immunological response of alpha thymosin peptides to act.

The following Table lists various antiviral agents of use in the invention with exemplary modes of action and exemplary dosages and modes of administration.

TABLE A

Antiviral Agents

| NAME | CHEMICAL CLASS | MODE OF ACTION[1] | TYPICAL DOSE[2] |
|---|---|---|---|
| Zidovudine (AZT) | Pyrimidine analog | Inhibits viral RNA-dependent DNA polymerase (reverse transcriptase); chain termination during DNA synthesis | 200 mg q4h |

TABLE A-continued

Antiviral Agents

| NAME | CHEMICAL CLASS | MODE OF ACTION[1] | TYPICAL DOSE[2] |
|---|---|---|---|
| Acyclovir | Purine analog | Inhibits DNA synthesis (DNA polymerase) Blocks chain elongation | 200 mg po q4h 5x/day for 10 days Topical |
| Ganciclovir | Purine analog | Inhibits DNA synthesis Inhibits DNA polymerase Prevents chain elongation | IV 5–10 mg/kg q8h IV 10 mg/kg per day |
| Vidarabine | Purine analog | Inhibits DNA Polymerase Prevents chain elongation | 15 mg/kg/day IV Ophthalmic oint. |
| Idoxuridine | Pyrimidine analog | Makes viral DNA more breakable | Ophth. oint. |
| Trifluridine | Pyrimidine analog | Inhibits DNA synthesis | Ophth. soln. |
| Foscarnet | Inorganic phosphonate | Inhibits viral DNA polymerase and reverse transcriptase | IV 90–120 mg/kg/day |
| Amantadine | Tricyclic amine | Blocks assembly of influenza virus | 200 mg/day |
| Rimantadine | Similar to Amantadine | Similar to Amantadine | 200–300 mg/day |
| Ribavirin | Purine analog | Multiple, including: Inhibits synthesis of guanine nucleotides Inhibits viral RNA polymerase Inhibits enzymes that cap mRNA | Aerosol 1.4 600–1800 mg/day mg/kg/hr 4000 mg/day IV po |
| Didanosine (ddI) | Purine analog | Blocks DNA chain elongation po Competitively inhibits reverse transcriptase | 125–200 mg bid |
| Zalcitabine (ddC) | Pyrimidine analog | Inhibits viral DNA synthesis Blocks DNA chain elongation Inhibits reverse transcriptase | 0.75 mg q8h po |

FIAU

[1] Mode of Action listed is exemplary of that generally known for each agent.
[2] Dosages provided are exemplary only. q4h = every four hours.
po = given orally.
q8h = every eight hours.
IV = intravenous
bid = given two times a day.

EXAMPLE 1

Treatment of Hepatitis C Infection in Human Patients

Efficacy of hepatitis C treatment is shown by evaluating the biochemical (ALT), virological (HCV DNA), serological (HceAg) and histological response in immune tolerant adult patients with chronic hepatitis C virus infection to treatment with Tα1 plus pegylated interferon and optionally ribavirin.

Efficacy Objectives

The primary endpoints will be the complete virological response rate defined as the percentage of patients with negative serum HCV DNA (as determined by the Chiron Quantiplex™ HCV DNA (cDNA) assay) and HCeAg at the end of 6-month treatment period and at the end of the 12-month follow-up period.

Safety Objectives

This study will evaluate safety data, including clinical status, hematological measures and measures of liver and kidney function, during the 6-month treatment period and for 12-month follow-up after the last administration of Tα1 plus pegylated interferon and optionally ribavirin.

Study Population

Criteria for Inclusion

1 Age≧18 yrs and ≦65 yrs.
2 Either male or female.
3 Documented evidence of the presence of HCsAg in the serum for at least six (6) months.
4 ALT<2.5 times the upper limit of normal on 2 determinations 4 weeks apart or the mean of 3 ALTs during the screening phase<2.5 times the upper limit of normal.
5 ALT<100 U/L during the screening phase.
6 HCV DNA>4,000 MEq/ml on 2 determinations≧4 weeks apart. If the second HCV DNA determination is ≦4,000 MEq/ml, a 3rd determination must be done 4 weeks after the 2nd. The 3rd determination must be >4,000 MEq/ml (as determined by the Chiron Quantiplex (cDNA) assay).
7 Positive HCeAg on 2 determinations≧4 weeks apart.
8 Liver biopsy within 12 months prior to enrollment consistent with chronic hepatitis.
9 Compensated liver disease with prothrombin time prolonged less than 5 sec over control, serum albumin≧30 g/L, bilirubin≦68 mmol/L.
10 Hematocrit≧30%, platelet count≧$100 \times 10^9$/L, WBC≧$3.5 \times 10^9$/L, and polymorphonuclear white cell count≧$1.7 \times 10^9$/L.
11 Adequate renal function:calculated creatinine clearance≧60 mL/min.
12 If a woman of child-bearing potential, use of an adequate method of contraception.

Criteria for Exclusion

1 Concomitant chronic use of any drug known to be hepatotoxic.
2 Concomitant chronic use of any immunosuppressive drug.
3 HIV infection diagnosed by HIV seropositivity and confirmed by Western blot.
4 Concomitant or prior history of malignancy other than curatively treated skin cancer or surgically cured in situ carcinoma of the cervix.
5 Active infectious process other than HCV that is not of a self-limiting nature. TB and AIDS are examples of infectious processes that are not of a self-limiting nature.
6 Cirrhosis.
7 A history of hepatic encephalopathy or bleeding esophageal varices.
8 Pregnancy documented by urine HCG pregnancy test.
9 Intravenous drug and alcohol abuse within the previous 5 years.
10 Patients who are poor medical or psychiatric risks or who have any non-malignant systemic disease that, in the opinion of the investigator, would make it unlikely that the patient could complete the protocol.

11 Simultaneous participation in another investigational drug study, or participation in any clinical trial involving experimental drugs within 30 days before study entry.
12 Any indication that the patient would not comply with the conditions of the study protocol.
13 Previous therapy with interferon or any other type of immunotherapy within 1 year of entry into the study or treatment with adrenocorticoid steroids within 6 months of entry into the study.
14 Any other liver disease including hepatitis B, hepatitis delta, alcoholic liver disease, drug-induced liver injury, primary biliary cirrhosis, sclerosing cholangitis, autoimmune hepatitis, hemochromatosis, α1 antitrypsin deficiency, or Wilson's disease.
15 Previous treatment with Tα1.
16 Previous treatment with interferon.
17 Previous treatment with ribavirin.
18 Patients with known hypersensitivity to Thymosin α1.
19 Patients with known hypersensitivity to interferon.
20 Patients with known hypersensitivity to ribavirin.

Conduct of Study

Screening Evaluation

All patients will undergo screening evaluation to determine eligibility for enrollment into the study. The evaluation consists of two, or on occasion three, separate screening visits. All data from screening visits will be recorded.

First Screening Visit (Screening Visit 1)

A. Eligibility

To be eligible for screening visit 1, the patient must have a history of chronic hepatitis as evidenced by a history of positive HCsAg for at least 6 months.

B. Screening Procedures

Laboratory screening tests at screening visit 1 will include hepatitis B antibody, hepatitis C antibody, hepatitis Delta antibody, HBV DNA, and ALT.

Complete history and physical examination.

Evaluate liver biopsy obtained within 12 months prior to enrollment.

Second Screening Visit

A. Eligibility

To be eligible to continue to screening visit 2, subjects must have positive HCsAg, HCeAg, and HCV DNA, and be negative for antibodies to hepatitis B and Delta.

B. Timing

Screening visit 2 will take place no less than 4 weeks after screening visit 1, and no more than 2 months after screening visit 1.

C. Screening Procedures

The following tests will be done at screening visit 2:
~Full blood count (FBC).Includes RBC, hematocrit, hemoglobin, WBC and differential counts
~Platelet count
~Prothrombin time (PT)
~Chemistry panel including BUN and creatinine
~ALT
~Serum albumin and total protein
~Bilirubin
~HceAg
~HCV DNA
~anti-HIV
~Ferritin
~Antinuclear antibody
~a-fetoprotein
~Urine pregnancy test Third Screening Visit (Screening Visit 3)

A. Eligibility

A third screening visit will be required only if the value of HCV DNA at screening 2 is ≦4,000 MEq/ml or if 1 of the ALT values at 1st or 2nd Screening is >2.5 times the upper limit of normal, and the other is <2.5 times the upper limit of normal.

B. Timing

Screening visit 3, if required, will take place no less than 4 weeks and no more than 2 months after screening visit 2.

C. Procedures

Laboratory tests at screening visit 3 will include HBV DNA, HCeAg, and ALT.

Study Enrollment

Following the screening evaluation, patients will be reviewed to determine if they meet the inclusion and exclusion criteria.

After informed consent is obtained Patients will be started on treatment ≦4 weeks from the completion of the screening evaluation.

Treatment Phase

Patients will receive treatment with:

Tα1 at 3.2 mg two times weekly (6 months). Peg-INFα2a at 180 μg subcutaneously (once daily, 6 months), or Interferon α at 1–3 MU subcutaneously (once daily, 6 months). Optionally ribavirin at 300 mg PO TID (three times daily, 6 months).

All subjects will have at least 12-months follow-up observation after completion of therapy.

Specific evaluations to be done during the treatment or observation portions of the study :

Month 0, 1, 3, 6 during treatment, then every 6 months for 12 months:
HCV DNA
HCeAg
Anti-HCe(only if HCeAg is negative)
HCsAg
Polyclonal HCsAg (only if HCsAg turned negative by monoclonal test)
Anti-HCc
Anti-HCs (only if HCsAg is negative)
Limited history and limited physical examination
Chemistry panel including: ALT (SGPT), AST (SGOT), alkaline phosphatase, total bilirubin, BUN and creatinine.
Hematology: RBC, hematocrit, WBC, differential, platelet count.
Prothrombin time
Urinalysis (specific gravity, glucose, protein, microscopic)
At month 18:
Repeat liver biopsy
Only at Week 0: urine pregnancy test (postmenarchal female subjects only).
Post-treatment Follow-up
Post-treatment follow-up will continue for a minimum of 12 months as specified above, collecting the data listed.

Definition of Time Limits

When testing every four weeks is required, patients are expected to return for scheduled clinic examinations and testing within one week of the day specified in the protocol. Missed visits, or visits made more than one week before or after the scheduled day, will be treated as protocol violations but these patients will not be excluded from data analysis. When testing is scheduled at approximately three-month intervals, testing should be done within 3 weeks of the specified date.

Study Medication, Supplies, and Packaging

Dosage and Administration

The dose of Tα1 will be standardized at 3.2 mg per injection for all treated patients.

PEG-INFα2a will be given at a dose of 180 μg once daily.

Ribavirin will optionally be given at a dose of 300 mg three times daily for six months.

Dosage Adjustments

No dosage adjustments are planned in this study.

Drug Supplies and Packaging

Synthetic Tα1, which has been formulated with mannitol and sodium phosphate, is manufactured by or for SciClone Pharmaceuticals in single-dose vials for injection. Vials will require reconstitution with sterile water for injection. The vials will be labeled with the drug name and dosage. This will be an open study.

PEG-INFα2a will be provided in conventional pharmaceutical compositions suitable for injection which include a pharmaceutically acceptable carrier, adjuvant, diluent, preservative and/or solubilizer. The single-dose vials will be labeled with the drug name and dosage.

Interferon α will be provided in conventional pharmaceutical compositions suitable for injection which include a pharmaceutically acceptable carrier, adjuvant, diluent, preservative and/or solubilizer. The single-dose vials will be labeled with the drug name and dosage.

Ribavirin will be provided as 300 mg tablets.

All drug supplies must be kept in a secure area, and dispensed only by pharmacists or other research members designated by investigators who have been approved for participation in this study.

Concomitant Medications and Lifestyle

Immunomodulatory drugs (except for the use of Tα1), glucocorticoids (such as prednisone), immunosuppressive drugs and drugs known to be hepatotoxic are prohibited.

No restrictions on other concomitant medications or lifestyle will be placed on the Patient; however, Patients will be discouraged from excessive use of alcoholic beverages.

Assessment of Compliance

Compliance with study medication dosing is defined as the Patient receiving≧80% of the scheduled amount or study medication each month.

Patients will return to the clinic for each injection of Tα1, and administration of the dose will be documented by the person administering it. At the discretion of the investigator, a patient who is likely to be highly compliant with the protocol may make arrangements for home, or self administration.

In cases of home administration of drug the patient and/or the patient's parent(s) and, if so desired, a designated health care worker will receive instructions on the process of self-injection or assisted injection by the study nurse. The study nurse will continue to administer the investigational drug until assured of the patient's ability to self-administer, or of the ability of a parent of designated assistant to provide the injections. The study nurse will communicate with the patient or parent each week and record compliance with the injections. The patient or parent will maintain a diary of the injections actually given, and of any adverse experiences.

Patients having home injections will be given appropriate container for disposal of used needles and syringes, and instructed in proper disposal techniques.

Discharging Patients from the Study

Criteria for Discharging Patients

1. Any treated patient who has an adverse reaction to treatment that threatens his/her well being will have treatment discontinued. The patient will be monitored for resolution of the adverse event and will continue to be monitored on the protocol schedule until completing the study.
2. Any patient who demonstrates a significant deterioration in his/her clinical status, in hematological parameters, or in biochemical tests of liver and/or renal function will be evaluated by the investigator and the monitoring committee. Evidence that would suggest such a deterioration includes:
    a) Progressive increases in ALT or AST over an interval of 6 months. Note that transient elevations in ALT and AST may precede a treatment-related or spontaneous remission, and are not a reason for discharging the patient from the study.
    b) Progressive increases in the total serum bilirubin levels over an interval of 6 months.
    c) Subjective increase in symptomatology so as to preclude the same level of daily activity as exercised by the patient at the time of inclusion.
    d) Hematologic and renal parameters outside the ranges listed in the inclusion criteria.
3. Any patient who withdraws voluntarily from the study.
4. Failure of patient, for whatever reason, to comply with study medication dosing defined as the Patient receiving <80% of the scheduled amount or study medication each month or failure to comply with other requirements of the protocol.
5. Withdrawal from the treatment is considered by the investigator to be in the patient's best interest.
6. The patient dies during the study.
7. The patient has completed entire combined 6-month treatment and 12-month follow-up period.

Procedure for Handling Dropouts

Patients removed from this study because of noncompliance with study medication dosing, defined as the Patient receiving<80% of the scheduled amount or study medication each month, will be replaced.

All Patients removed from the study will continue to be followed, and their clinical course included in the final report.

Adverse Experiences

Documenting Adverse Experiences

Adverse event information will be documented during the entire combined 6-month treatment and 12-month follow-up period. Any adverse events continuing at the time of the last scheduled visit will be followed until they are resolved or explained or until the event stabilizes and the overall clinical outcome has been ascertained.

Patients will be monitored for significant side-effects or allergic manifestations possibly resulting from treatment. Although no local or systemic side effects have been observed with Tα1, the injections will be terminated if systemic hypersensitivity reactions such as urticaria or wheezing occur. Patients will be educated on the symptoms of severe anaphylactic reactions and informed of appropriate countermeasures.

All patients will be requested to report on any problems emerging since the previous visit. To avoid observer bias, all patients will be asked by non-directed questions about adverse events throughout the study. Non-directed questions include "Have you had any problems since your last visit?" When problems are described, they will be pursued in greater detail. The investigator will determine if the adverse event can reasonably be related to the study medication. All adverse events will be recorded, including date of onset, duration, and severity.

Assessment of Severity of Adverse Experiences

The severity of adverse events will be designated as mild, moderate, or severe as follows:

| | |
|---|---|
| Mild | No clinical significance, no requirement for additional assessment |
| Moderate | Event presented a problem, but did not affect daily activities or clinical status |
| Severe | Event resulted in marked alteration of daily activities or clinical status |

In addition to classifying the adverse event as mild, moderate, or severe the Investigator should determine whether or not an event is serious. The regulatory definition of a serious event includes those that are fatal, life-threatening (e.g., anaphylaxis), severely or prematurely disabling or incapacitating, or events resulting in or prolonging inpatient hospitalization, congenital anomaly, cancer, or a drug overdose (whether accidental or intentional).

Assessment of Causality

Every effort should be made by the investigator to explain each adverse experience and assess its relationship, if any, to study drug treatment. Causality should be assessed using the following categories: unrelated, probably related, possibly related, related.

The degree of certainty with which an adverse experiences is attributed to drug treatment (or alternative causes, e.g., natural history of the underlying diseases, concomitant therapy, etc.) will be determined by how well the experience can be understood in terms of one or more of the following:

1. Known pharmacology of the drug.
2. Reaction of similar nature being previously observed with this drug or class of drug.
3. The experience having often been reported in literature for similar drugs as drug related e.g. skin rashes, blood dyscrasia.
4. The experience being related by time to drug ingestion terminating with drug withdrawal (dechallenge) or reproduced on rechallenge.

Follow-up of Adverse Experiences

Investigators should follow-up subjects with adverse experiences until the event has subsided (disappeared) or until the condition has stabilized. Reports relative to the subject's subsequent course must be submitted to the clinical study monitor.

Overdose

Any instance of overdose (suspected or confirmed) must be communicated to the investigator within 24 hours and be fully documented as a serious adverse experience. Details of any signs or symptoms and their management should be recorded including details of any antidote(s) administered.

Pregnancy

Subjects who become pregnant during the study should discontinue treatment immediately.

Subjects should be instructed to notify the investigator if it is determined after completion of the study that they become pregnant either during treatment or within 30 days after the end of treatment.

Whenever possible a pregnancy should be followed to term, any premature terminations reported, and the status of the mother and child should be reported after delivery.

Administrative Requirements

Review and Consent Requirements

Ethical Review Committee

The sponsor will supply all necessary data to the investigator for submission to the Ethics Committee (Institutional Review Board) at the investigator's institution.

Ethics and Informed Consent

All patients will sign informed consent forms approved by the hospital Institution Review Board. The form will state the nature of the research study, the type of treatment options, the nature of samples to be obtained, and the possible risks and benefits. The investigator or his designee will obtain informed consent after ascertaining that the patient fully understand the contents of the consent form. A copy of the signed consent form will be given to the patient. Patient confidentiality will be maintained throughout the study, and patients will be identified on case report forms only by assigned study identification numbers.

Procedures and Possible Risks

Venipuncture and Phlebotomy

Patients will have approximately 30 ml of blood drawn prior to entry into the study, approximately monthly initially and every three months for the remainder of the study. For smaller patients, efforts will be made to draw only the minimum amount of blood required for the tests listed in this protocol. The blood loss resulting from this testing is not felt to be significant in the patients who will meet the criteria for inclusion in this study. Risk of venipuncture and phlebotomy will be minimized by use of an experienced person to carry out these procedures, and further minimized by use of aseptic technique.

Liver Biopsy

Patients would have percutaneous liver biopsy performed before the entry into the study and at the end of the 12 months follow-up period. Liver biopsy would be performed by experienced hepatologist. The incidence of complications is less than 5% and this includes pain at the site of entry, hemorrhage, bile peritonitis, pneumothorax, penetration of abdominal viscera and sepsis. The mortality rate is less than 0.1%.

Laboratory

Laboratory studies will be conducted by a certified laboratory of the investigator's choosing. Investigators should employ the same laboratory during the entire study. The investigator will supply the sponsor with a copy of the laboratory's current certification, a list of the test methods used, and a list of normal ranges for the tests included in the protocol. When appropriate, normal values should be listed on age and sex. These must be provided at the onset of the study, and will be used to interpret results obtained in the study. If it is necessary to change laboratories during the study, or if the laboratory changes methodology or normal values, patient records must have the data of these changes noted. When possible, laboratory methods should not be changed during the course of the study.

For certain tests the sponsor may wish to specify a particular testing laboratory. For instance, determination of HCV DNA may be such a test. This will be negotiated with the investigator.

Data Evaluation

Criteria for Efficacy

Primary Endpoints

The primary endpoints will be the complete virological response rate defined as the percentage of the patients with negative HCV DNA (as determined by the Chiron Quantiplex™ HCV DNA (cDNA) assay) and HCeAg at the end of the 6-month treatment period and at the end of the 12-month follow-up period.

Secondary Endpoints

1. The percentage change from baseline in the levels of HCV DNA at the end of the 6-month treatment and 12-month follow up period;
2. The proportion of patients who have a reduction in their ALT levels to below the upper limit of the normal range at the end of treatment period and at the end of the 12 month follow up period;
3. The proportion of patients with loss of hepatitis C s antigen at the end of the treatment period and at the end of the 12 month follow up period;
4. The proportion of patients with an improvement in Knodell score of liver histology.

Safety Evaluation

The clinical assessments and frequent blood testing will provide a mechanism to monitor patients for drug safety and to minimize the risk of undiscovered adverse reactions.

Statistical Assessment

Analysis

Data will be analyzed by the investigators, and also by SciClone Pharmaceuticals, or by its statistical consultants. Data will be tested for normality, skewness, and heterogeneity of variances. If needed, data will be transformed using logarithmic function.

Analyses will include:
~description and analyses of such demographic variables as age and sex.
~baseline characteristics such as medical history and physical exam.

All significance testing will be done using two-tailed tests, and statistical significance will be based upon an alpha level of 0.05. Data listings, cross tabulations, and graphics will be used appropriately to support the analyses and the narrative report.

Safety Analysis

Safety assessment will be based upon analysis of observed clinical, local, or systemic effects. The incidence of abnormalities of each laboratory results will be presented. Laboratory abnormalities of individual patients will be reviewed by the medical monitor according to specified criteria.

Subgroup Analysis

The following subgroups will be identified, and their results analyzed. The results may not, depend upon the number of patients in each group, be statistically significant. In such instance, the information may be used as a guide to future studies:

1. Male patients; female patients
2. Liver biopsy
   ~patients showing minimal changes
   ~patients showing chronic persistent hepatitis
   ~patients showing chronic active hepatitis
3. Known duration of the patient's carrier state.
4. Patient age.

EXAMPLE 2

The effects of 3 different doses of thymalfasin (TA1) in combination with PEG-IFN2a on week 12 HCV RNA levels and T cell counts was investigated.

Patients with chronic hepatitis C who were non-responders to previous antiviral therapy were randomized to receive PEG-IFN2a 180 µg/week plus thymalfasin given twice a week by subcutaneous injection (Group 1, 0.8 mg; Group 2, 1.6 mg; Group 3, 3.2 mg). In order to assess effect of thymalfasin on PEG-IFN2a, patients were included only if they were infected with HCV genotype 1 and had serum HCV RNA levels greater than 2 million copies per ml. The effect of therapy was assessed on the reduction in serum HCV RNA after 12 weeks, early virologic response (EVR, proportion which greater than 2 log reduction or negative HCV RNA by the Roche Amplicor assay) and on changes in peripheral CD3 and CD4 lymphocyte counts from baseline (assessed by flow cytometry).

31 patients (26 male) with median age 47 yrs (range 39–58) were enrolled. Four were non-responders to a previous course of standard IFN alone while 27 had previously non responded to standard IFN with ribavirin. All subjects completed 12 weeks of therapy. Six (19%) became negative for HCV RNA on therapy. Thymalfasin was well tolerated with no obvious side effects. The median reduction in HCV RNA increased with dose with thymosin (Table B).

TABLE B

| Group | No. | Dose T1 (mg biw) | Median Reduction HCV RNA (log) | EVR | CD3+ | CD4+ |
| --- | --- | --- | --- | --- | --- | --- |
| 1 | 10 | 0.8 | 0.57 | 20% | 0% | −0.2% |
| 2 | 10 | 1.6 | 0.97* | 30% | +8.3% | +14.8% |
| 3 | 11 | 3.2 | 1.09** | 36% | +7.5% | +8.8% |

**p < 0.005 vs group 1;
*p < 0.01 vs group 1;
EVR, early virologic response.

These data show a dose-response effect of thymalfasin in combination with PEG-IFN2a in high viral load non-responders infected with HCV genotype 1. The mechanisms of action of thymalfasin may be related to the observed shift in the proportion of CD3 and CD4 positive T cells in the circulation.

Close to half of all patients fail to respond to initial treatment with currently available therapies and become non-responders. TA1 in combination with pegylated interferon alpha increased early virologic response (EVR) rates up to 36% in hepatitis C patients who had failed prior therapy. Complete data from the twelve week dose ranging study showed that groups of non-responders treated with TA1 combination therapy reported positive dose related EVR rates ranging from 20 to 36%. EVR is suggested to be an early indicator of sustained response, and non-responders seldom have a sustained response to re-treatment.

These data suggest that TA1 in combination with pegylated interferon may be able to treat a large subset of hepatitis C patients that have been extremely difficult to treat in the past non-responders infected with hepatitis C genotype 1. TA1 was well tolerated with no obvious side effects.

These data indicate that TA1 has the potential to offer new, safer and better therapy options for hepatitis C patients. Twelve week EVR data has been proposed by hepatologists to be a predictor of patients that may or may not respond to pegylated interferon therapy. Significantly, the twelve week data from this dose ranging study clearly show TA1's ability to add to the antiviral effects of pegylated interferon and improve response rates in the treatment of some of the most difficult to treat hepatitis C patients, those who have already failed to respond to prior therapy.

Close to half of all hepatitis C patients fail to respond to the standard therapy of pegylated interferon plus ribavirin. More dramatically, an estimated two million hepatitis C carriers in the U.S. are infected with a high viral load of genotype 1 virus and are the most difficult group of patients to treat. In comparison to the general hepatitis C patient population, 70% of these patients fail to respond to standard therapy.

All 31 hepatitis C patients in the dose ranging study had a high viral load of genotype 1 virus, 27 having failed previous treatment with interferon plus ribavirin and four having failed with interferon alone. Patients were randomized into three groups to receive 180 mcg/week of pegylated interferon alpha-2a plus one of three different bi-weekly doses of TA1.

Observation at the end of 12 weeks of therapy showed that EVR (measured by negative or a greater than 2 log reduction in hepatitis C viral RNA) increased with higher doses of TA1. The groups receiving 0.8 mg, 1.6 mg and 3.2 mg doses of TA1 in combination therapy reported EVR rates of 20%, 30% and 36%, respectively.

EXAMPLE 3

A 47-year old woman presented with symptoms of severe fatigue and fever about 6 weeks after facial plastic surgery. Her liver enzymes showed an ALT of 500 IU per ml. A HCV RNA level was ordered and returned with a viral load of 860,000 with HCV genotype-1a found. Her bilirubin was 2.0 mg/dl and all other liver function tests were normal including albumin and INR. Her AST, AP and GGT were mildly elevated. The patient underwent a liver biopsy to look for evidence of chronic liver disease and stage 0–1 fibrosis was noted but the grade of the inflammation was 3.

Her somatic symptoms worsened and she was started on Interferon (INF) and ribavirin. At 3 months her ALT was 20 IU/ml and her bilirubin was normal. She was severely fatigued on treatment, yet manic and triple sleeping medications were required. HCV RNA levels were less than 550 IU/ml throughout the course of treatment and at the end of treatment. After stopping INF and ribavirin her liver enzymes increased to 300 IU/ml and her HCV RNA went to 220,000 IU/Ml and all of her severe somatic symptoms returned. She was not able to work.

Then it was decided to start PEG Intron at ⅕ mc/kg/w, ribavirin at 12 mg/kg/day and thymosin-alpha-1 at 3.2 mcg BIW SQ, as a second course of treatment. The HCV RNA blood levels decreased to less than 5 IU/mL by TMA at month 1, 3, 6 and 12. Therapy was discontinued at 12 months and the HCV RNA was also negative by TMA at 1 and 3 months after stopping therapy.

The patient had to be kept on Zyprexa through the second course of treatment due to mania, but this symptom was very similar to the first course and much better controlled without the use of sleeping medications. Currently the patient is fully functional, with normal liver enzymes and without symptoms.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A method of treating hepatitis C comprising administering to a hepatitis C patient an effective amount of at least one alpha thymosin peptide, in combination with administration to said hepatitis C patient of an effective amount of at least one pegylated interferon and an antiviral-effective amount of ribavirin, wherein said patient is a non-responder to previous interferon treatment.

2. The method of claim 1, wherein said peptide is thymosin alpha 1 (TA1).

3. The method of claim 2, wherein said TA1 is administered in a dose from about 500 to about 4500 micrograms.

4. The method of claim 1, wherein said pegylated interferon comprises pegylated interferon α-2a.

5. The method of claim 4, wherein said pegylated interferon is administered at a dose between about 0.25–250 μg.

6. The method of claim 1, wherein said pegylated interferon comprises at least one interferon conjugated to at least one polyethylene glycol (PEG).

7. The method of claim 1, wherein said amount of ribavirin is a dose of between about 100 mg and 2000 mg.

* * * * *